(12) United States Patent
Bonn et al.

(10) Patent No.: US 8,355,803 B2
(45) Date of Patent: Jan. 15, 2013

(54) PERFUSED CORE DIELECTRICALLY LOADED DIPOLE MICROWAVE ANTENNA PROBE

(75) Inventors: Kenlyn S. Bonn, Boulder, CO (US); Ian S. Smith, Boulder, CO (US)

(73) Assignee: Vivant Medical, Inc., Boulder, CO (US)

( * ) Notice: Subject to any disclaimer, the term of this patent is extended or adjusted under 35 U.S.C. 154(b) by 559 days.

(21) Appl. No.: 12/561,096

(22) Filed: Sep. 16, 2009

(65) Prior Publication Data

US 2011/0066144 A1 Mar. 17, 2011

(51) Int. Cl.
*A61B 18/18* (2006.01)

(52) U.S. Cl. .............................. 607/156; 606/33; 606/41

(58) Field of Classification Search .................... 606/33, 606/41; 607/156
See application file for complete search history.

(56) References Cited

U.S. PATENT DOCUMENTS

| | | | |
|---|---|---|---|
| 3,631,363 A | 12/1971 | Miller | |
| 4,397,313 A | 8/1983 | Vaguine | |
| 4,462,412 A | 7/1984 | Turner | |
| 4,572,190 A | 2/1986 | Azam et al. | |
| 4,744,372 A | 5/1988 | Kikuchi et al. | |
| 4,791,930 A * | 12/1988 | Suzuki et al. | 607/96 |
| 4,798,215 A | 1/1989 | Turner | |
| 5,097,844 A | 3/1992 | Turner | |
| 5,275,597 A | 1/1994 | Higgins et al. | |
| 5,366,490 A | 11/1994 | Edwards et al. | |
| 5,370,675 A | 12/1994 | Edwards et al. | |
| 5,417,210 A | 5/1995 | Funda et al. | |
| 5,470,308 A | 11/1995 | Edwards et al. | |
| 5,536,240 A | 7/1996 | Edwards et al. | |
| 5,599,294 A | 2/1997 | Edwards et al. | |
| 5,607,389 A | 3/1997 | Edwards et al. | |
| 5,620,480 A | 4/1997 | Rudie | |
| 5,643,197 A * | 7/1997 | Brucker et al. | 604/20 |
| 5,720,718 A | 2/1998 | Rosen et al. | |
| 5,944,749 A | 8/1999 | Fenn | |
| 6,031,375 A | 2/2000 | Atalar et al. | |
| 6,067,475 A | 5/2000 | Graves et al. | |
| 6,097,985 A | 8/2000 | Kasevich et al. | |

(Continued)

FOREIGN PATENT DOCUMENTS

DE 390937 3/1924

(Continued)

OTHER PUBLICATIONS

U.S. Appl. No. 10/244,346, filed Sep. 16, 2002, Abandoned.

(Continued)

*Primary Examiner* — Linda Dvorak
*Assistant Examiner* — Jocelyn D Ram (57) ABSTRACT

A microwave surgical ablation probe having an arrangement of coolant channels in fluid communication with a cooling chamber disposed within the distal end of the probe is disclosed. A hypotube having one or more longitudinal ribs extending radially inward from an inner surface thereof is coaxially disposed around a coaxial feedline. The longitudinal ribs of the hypotube engage an outer sheath of the feedline to define a fluid inflow channel to deliver coolant to the cooling chamber, and a fluid outflow channel to receive fluid from the cooling chamber. The cooling chamber may be formed from porous ceramic or porous metallic material that provides structural support to the probe while permitting coolant to circulate therethrough. The probe includes dielectric and choke members that are adapted to control the microwave radiation pattern (e.g., ablation shape), and which may provide improved coupling of the probe to tissue.

18 Claims, 5 Drawing Sheets

U.S. PATENT DOCUMENTS

| | | |
|---|---|---|
| 6,181,970 B1 | 1/2001 | Kasevich |
| 6,233,490 B1 | 5/2001 | Kasevich |
| 6,275,738 B1 | 8/2001 | Kasevich et al. |
| 6,289,249 B1 | 9/2001 | Arndt et al. |
| 6,312,391 B1 | 11/2001 | Ramadhyani et al. |
| 6,334,074 B1 | 12/2001 | Spertell |
| 6,375,606 B1 | 4/2002 | Garibaldi et al. |
| 6,413,255 B1 | 7/2002 | Stern |
| 6,419,653 B2 | 7/2002 | Edwards et al. |
| 6,451,015 B1 | 9/2002 | Rittman, III et al. |
| 6,512,956 B2 | 1/2003 | Arndt et al. |
| 6,592,579 B2 | 7/2003 | Arndt et al. |
| 6,603,994 B2 | 8/2003 | Wallace et al. |
| 6,610,054 B1 | 8/2003 | Edwards et al. |
| 6,675,050 B2 | 1/2004 | Arndt et al. |
| 6,725,080 B2 | 4/2004 | Melkent et al. |
| 6,807,444 B2 | 10/2004 | Tu et al. |
| 6,847,848 B2 | 1/2005 | Sterzer et al. |
| 6,852,091 B2 | 2/2005 | Edwards et al. |
| 6,866,624 B2 | 3/2005 | Chornenky et al. |
| 6,944,504 B1 | 9/2005 | Arndt et al. |
| 7,008,421 B2 | 3/2006 | Daniel et al. |
| 7,377,917 B2 | 5/2008 | Trembly |
| 7,387,626 B2 | 6/2008 | Edwards et al. |
| 7,439,736 B2 | 10/2008 | Meaney et al. |
| 7,467,015 B2 | 12/2008 | Van der Weide |
| 7,565,207 B2 | 7/2009 | Turner et al. |
| 7,642,451 B2 | 1/2010 | Bonn |
| 7,875,024 B2 | 1/2011 | Turovskiy et al. |
| 7,998,139 B2 * | 8/2011 | Rossetto et al. ............... 606/33 |
| 8,035,570 B2 | 10/2011 | Prakash et al. |
| 8,059,059 B2 | 11/2011 | Bonn |
| 8,118,808 B2 | 2/2012 | Smith et al. |
| 2002/0022836 A1 | 2/2002 | Goble et al. |
| 2003/0065317 A1 | 4/2003 | Rudie et al. |
| 2004/0097805 A1 | 5/2004 | Verard et al. |
| 2004/0242992 A1 | 12/2004 | Hareyama |
| 2005/0015082 A1 * | 1/2005 | O'Sullivan et al. ............ 606/41 |
| 2005/0222564 A1 * | 10/2005 | Plaza .............................. 606/41 |
| 2005/0228370 A1 | 10/2005 | Sterzer et al. |
| 2005/0245920 A1 * | 11/2005 | Vitullo et al. .................. 606/33 |
| 2007/0078453 A1 | 4/2007 | Johnson et al. |
| 2007/0185554 A1 | 8/2007 | Appling et al. |
| 2007/0282319 A1 | 12/2007 | van der Weide et al. |
| 2007/0288079 A1 | 12/2007 | van der Weide et al. |
| 2009/0222002 A1 * | 9/2009 | Bonn et al. ..................... 606/33 |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 481 685 | 4/1992 |
| EP | 0 521 264 | 1/1993 |
| EP | 0 541 930 | 5/1993 |
| EP | 0 556 705 | 8/1993 |
| EP | 0 558 429 | 9/1993 |
| EP | 0 572 131 | 12/1993 |
| EP | 0 836 868 | 4/1998 |
| EP | 1 159 926 | 5/2001 |
| EP | 1 278 007 | 1/2003 |
| EP | 1 810 627 | 7/2007 |
| FR | 179607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | WO97/41924 | 11/1997 |
| WO | WO97/43971 | 11/1997 |
| WO | WO00/48672 | 8/2000 |
| WO | 00/53113 | 9/2000 |
| WO | WO00/51513 | 9/2000 |
| WO | WO01/01847 | 1/2001 |
| WO | WO01/74252 | 10/2001 |
| WO | WO02/45790 | 6/2002 |
| WO | WO02/061880 | 8/2002 |
| WO | WO2004/112628 | 12/2004 |
| WO | WO2005/016119 | 2/2005 |
| WO | WO2007/112081 | 10/2007 |

OTHER PUBLICATIONS

U.S. Appl. No. 12/023,606, filed Jan. 31, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.

U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
180. B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Cosman et al., "Methods of Making Nervous System Lesions" in William RH, Rengachary SS (eds): Neurosurgery, New York: McGraw Hill, vol. 111, (1984), pp. 2490-2499.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline Product Literature, "Light Key: Visualize a Virtual Keyboard. One With No Moving Parts", 4 pages.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.
Jarrett et al., "Use of the LigaSure™ Vessel Sealing System for Peri-Hilar Vessels in Laparoscopic Nephrectomy" Sales/Product Literature 2000.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008, Abstract only.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Mar. 2000) I'D Wire: product description, 1 page.
MDTECH product literature (Dec. 1999) "FlexStrand": product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences—Yingyong Kexue Xuebao, Shangha CN, vol. 23, No. 2:(Mar. 2005); pp. 160-184 Abstract only.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Oapril 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).

Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Vessel Strasberg et al., "Use of a Bipolar Vessel Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
S. Humphries Jr. et al., "Finite-Element Codes to Model Electrical Heating and Non-Linear Thermal Transport in Biological Media", Proc. ASME HTD-355, 131 (1997).
Urologix, Inc.-Medical Professionals: Targis™ Technology (Date Unknown). "Overcoming the Challenge"located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984)pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.

European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
Esterline Product Literature, "Light Key: Visualize a Virtual Keyboard. One With No Moving Parts", Nov. 1, 2003; 4 pages.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.
European Search Report EP 06024123 dated Mar. 6, 2007.
European Search Report EP 07019173 dated Feb. 12, 2008.
European Search Report EP 07019174 dated Jan. 29, 2008.

* cited by examiner

PERFUSED CORE DIELECTRICALLY LOADED DIPOLE MICROWAVE ANTENNA PROBE

BACKGROUND

1. Technical Field

The present disclosure relates to systems and methods for providing energy to biological tissue and, more particularly, to a microwave ablation surgical probe having a porous core through which coolant is circulated and methods of use and manufacture therefor.

2. Background of Related Art

Energy-based tissue treatment is well known in the art. Various types of energy (e.g., electrical, ultrasonic, microwave, cryogenic, thermal, laser, etc.) are applied to tissue to achieve a desired result. Microwave energy can be delivered to tissue using an antenna probe. Presently, there are several types of microwave probes in use, e.g., monopole, dipole, and helical. One type is a monopole antenna probe, which consists of a single, elongated microwave conductor exposed at the end of the probe. The probe is typically surrounded by a dielectric sleeve. The second type of microwave probe commonly used is a dipole antenna, which consists of a coaxial construction having an inner conductor and an outer conductor with a dielectric junction separating a portion of the inner conductor. The inner conductor may be coupled to a portion corresponding to a first dipole radiating portion, and a portion of the outer conductor may be coupled to a second dipole radiating portion. The dipole radiating portions may be configured such that one radiating portion is positioned proximally of the dielectric junction, and the other portion is positioned distally of the dielectric junction. In monopole and dipole antenna probes, microwave energy generally radiates perpendicularly from the axis of the conductor.

A typical microwave antenna has a long, thin inner conductor that extends along the axis of the probe and is surrounded by a dielectric material and is further surrounded by an outer conductor around the dielectric material such that the outer conductor also extends along the axis of the probe. In another variation of the probe that provides for effective outward radiation of energy or heating, a portion or portions of the outer conductor can be selectively removed. This type of construction is typically referred to as a "leaky waveguide" or "leaky coaxial" antenna. Another variation on the microwave probe involves having the tip formed in a uniform spiral pattern, such as a helix, to provide the necessary configuration for effective radiation. This variation can be used to direct energy in a particular direction, e.g., perpendicular to the axis, in a forward direction (i.e., towards the distal end of the antenna), or combinations thereof.

Invasive procedures and devices have been developed in which a microwave antenna probe may be either inserted directly into a point of treatment via a normal body orifice or inserted percutaneously. Because of the small difference between the temperature required for denaturing malignant cells and the temperature injurious to healthy cells, a known heating pattern and predictable temperature control is important so that heating is confined to the tissue to be treated. For instance, hyperthermia treatment at the threshold temperature of about 41.5° C. generally has little effect on most malignant growth of cells. However, at slightly elevated temperatures above the approximate range of 43° C. to 45° C., thermal damage to most types of normal cells is routinely observed.

One approach to controlling probe and/or tissue temperature is to circulate coolant within the probe to extract excess heat from the probe. However, providing coolant passages within a probe may reduce probe strength, because such passages necessitate the introduction of voids into the probe structure.

In some surgical procedures, a microwave antenna probe may be inserted percutaneously into, for example, a chest wall of a patient. During such a procedure, negotiating the probe through, for example, fibrous thoracic tissue and ribs may place undue stresses on the probe. Additionally, a cooled probe may lack sufficient strength to withstand the stresses imposed by such percutaneous insertions, which may result in probe failure.

SUMMARY

The present disclosure provides a high-strength electromagnetic surgical ablation probe that includes a cooled and dielectrically buffered antenna assembly. A cable provides electromagnetic energy to the probe via a coaxial conductor and/or provides coolant via a fluid conduit to improve power delivery performance and power handling, and to reduce component temperatures. Suitable coolants include deionized water, sterile water, or saline.

The disclosed ablation probe includes a coaxial feedline having in coaxial arrangement an outer sheath, an outer conductor, an inner conductor, and a dielectric disposed between the outer conductor and the inner conductor. The inner conductor extends distally beyond the outer sheath, the outer conductor, and the dielectric, e.g., the outer layers of the feedline may be stripped leaving the inner conductor extending distally. A hypotube is coaxially disposed around the feedline. The hypotube includes one or more longitudinal ribs extending radially inward from an inner surface of the hypotube. The ribs extend from the inner surface of the hypotube to an outer surface of the feedline to define one or more fluid channels between the feedline and the hypotube. During manufacture, the ribs may be formed in the hypotube by being drawn into the tubing, extrusion, and/or formed by welding two or more semicircular "clamshell" halves of the hypotube together.

A feed point seal joins a distal end of the hypotube to a porous core enclosed within the probe distal radiating section. The feed point seal includes one or more an openings defined therethrough to provide a fluid path between the fluid channels and the porous core. The feed point seal includes an opening, which may be axially positioned, to enable the inner conductor to pass therethough, e.g., to extend distally into the porous core. The feed point seal additionally or alternative seals one or more conductors of the feedline, which may help prevent coaxial feedline short circuiting (e.g., shorts between conductors and/or other elements of the probe).

A microwave ablation antenna in accordance with the present disclosure may be configured to operate in a range of about 915 MHz to about 2.45 GHz, or within any other suitable frequency range. In one embodiment, the hypotube ribs press into the coaxial cable thereby forming a separate fluid inflow channel and fluid outflow channel. A coolant, such as saline or dionized water, is introduced into a proximal end of the inflow channel, from where it flows distally, through openings in the feed point seal into a radiating section that includes a radiating section having a porous core. The porous core is perfused with coolant, which may help to reduce probe temperatures, and may provide improved dielectric coupling between the probe and tissue. The dual-chamber design of the disclosed probe may provide better coolant dispersion within the probe, thereby providing increased coolant efficiency, and allowing the size of the probe to be greatly reduced.

The porous perfused core may include a separator to define a two chamber perfusion arrangement wherein coolant would first travel distally past the distal radiating section through an inflow chamber region, then return proximally through an outflow chamber region. The porous core may be formed from porous ceramic, porous metal, or any suitable material that permits coolant fluid to circulate. Additionally, the porous core may add strength to the dielectric surface of the probe.

A dielectric coating may enclose the entire probe and act as the dielectric match between the probe and tissue The coating may act as a sealing layer for the entire probe, and may be formed from lubricious material to facilitate the insertion of the probe percutaneously into tissue.

Also disclosed is a microwave ablation system that includes a source of ablation energy, e.g., a microwave generator, that is operably coupled to a perfused core dielectrically loaded dipole microwave antenna probe as described herein. The disclosed system may include a source of coolant operably coupled to the probe, e.g., to the hypotube.

Also disclosed is a method of manufacturing a perfused core dielectrically loaded dipole microwave antenna probe that includes the steps of providing a hypotube having one or more longitudinal ribs extending radially inward from an inner surface thereof. A coaxial feedline is provided. The coaxial feedline has, in coaxial arrangement, an outer sheath, an outer conductor, an inner conductor, and a dielectric disposed between the outer conductor and the inner conductor. The inner conductor extends distally beyond the outer sheath, the outer conductor, and the dielectric. The inner conductor may be extended by, for example and without limitation, stripping the outer layers of the coaxial feedline to expose the inner conductor. The hypotube is mounted over the feedline to form a fluid channel between the inner surface of the hypotube, the one or more ribs, and an outer surface of the feedline. A feed point seal is overmolded at a distal end of at least one of the hypotube, the sheath, the outer conductor, or the dielectric, and the porous core is mounted to a distal end of the feed point seal.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure will be described hereinbelow with reference to the accompanying drawings; however, it is to be understood that the disclosed embodiments are merely exemplary of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, shall refer to the end of the instrument that is closer to the user, while the term "distal" shall refer to the end that is farther from the user.

Figure 1:
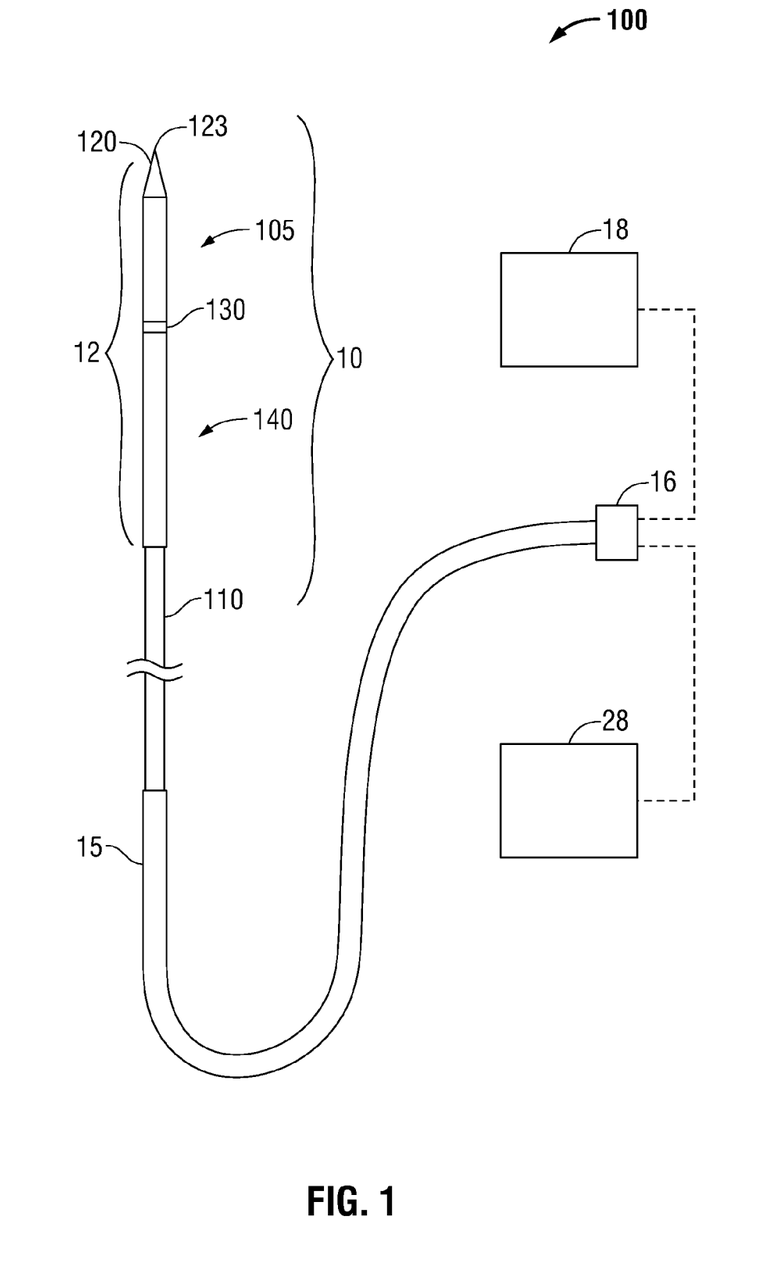
FIG. 1 shows a diagram of a microwave ablation system having a cooled electromagnetic surgical ablation probe in accordance with an embodiment of the present disclosure.

FIG. 1 shows an embodiment of a microwave ablation system 100 in accordance with the present disclosure. The microwave ablation system 100 includes an ablation probe 10 connected by a cable 15 to connector 16, which may further operably connect the probe 10 to a generator assembly 28. Probe 10 includes a proximal radiating section 140 and a distal radiating section 105. Distal radiating portion 105 of radiating portion 12 includes a tapered end 120 which terminates at a tip 123 to allow for insertion into tissue with minimal resistance. Alternatively, tip 123 may be rounded or flat, and may include a forceps or a blade. Generator assembly 28 may be a source of ablation energy, e.g., microwave energy in the range of about 915 MHz to about 2.45 GHz. Cable 15 may additionally or alternatively provide a conduit (not explicitly shown) configured to provide coolant from a coolant source 18 to the ablation probe 10.

Figure 2:
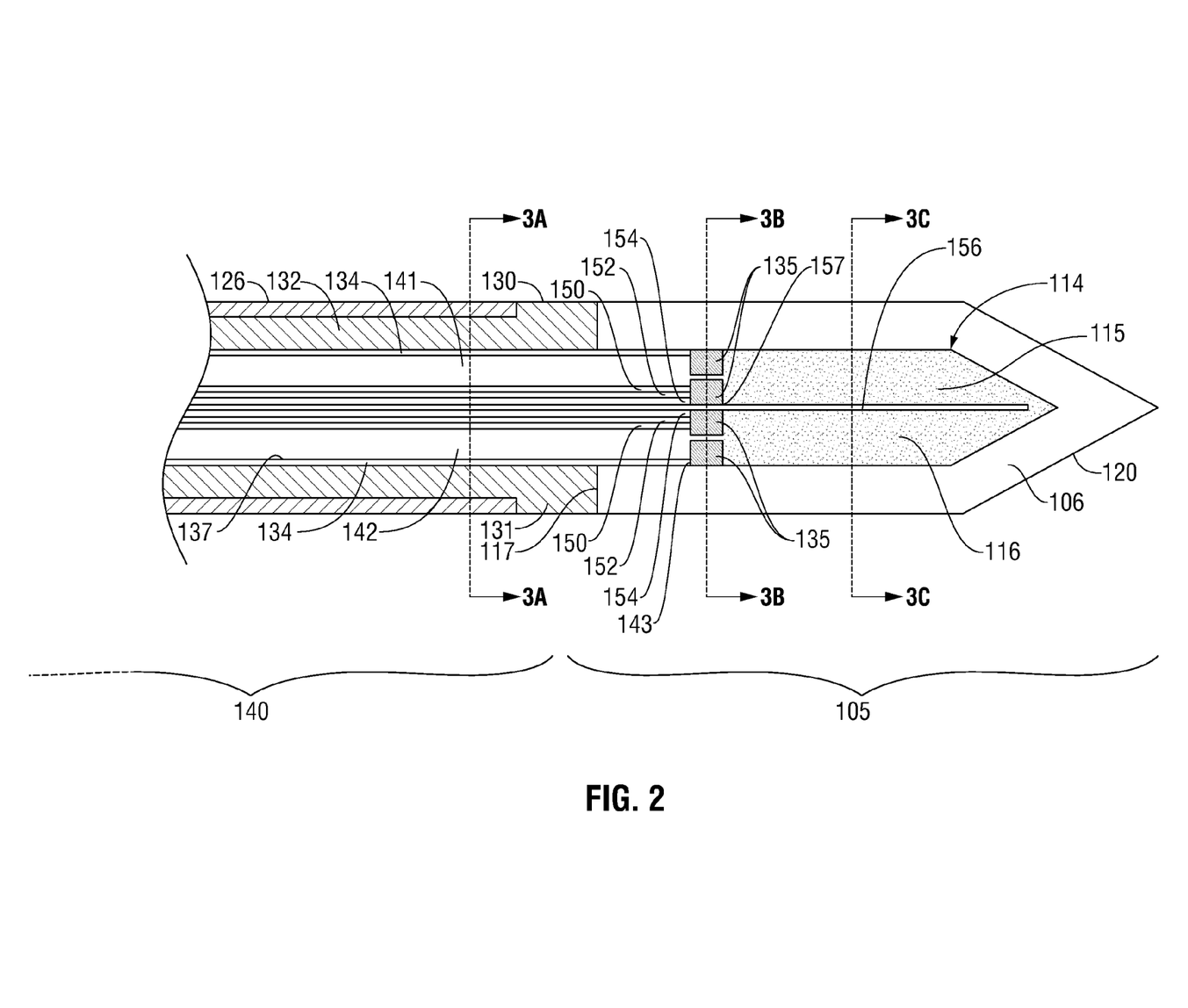
FIG. 2 shows a cross sectional view of an embodiment of a cooled surgical ablation probe in accordance with the present disclosure.

With additional reference to FIG. 2, an embodiment of an ablation probe 100 includes a coaxial feedline 110 that extends from a proximal end of the probe 10, which may include a handle (not explicitly shown), wherein the coaxial feedline 110 is adapted to provide radiofrequency and/or microwave ablation energy to the probe 10 generally, and more specifically, to proximal radiating portion 140 and distal radiating portion 105. Coaxial feedline 110 may exhibit an impedance of 50Ω. Coaxial feedline 110 includes, in coaxial arrangement, an outer coaxial conductor 152, a dielectric layer 154 coaxially disposed within outer coaxial conductor 152, and an inner conductor 156 coaxially disposed within dielectric layer 154. Inner conductor 156 of coaxial feedline 110 extends distally through a feed point seal 135 into porous core 114, as will be described further hereinbelow. An insulating outer sheath 150 may be coaxially disposed around outer coaxial conductor 152.

Figure 3A:
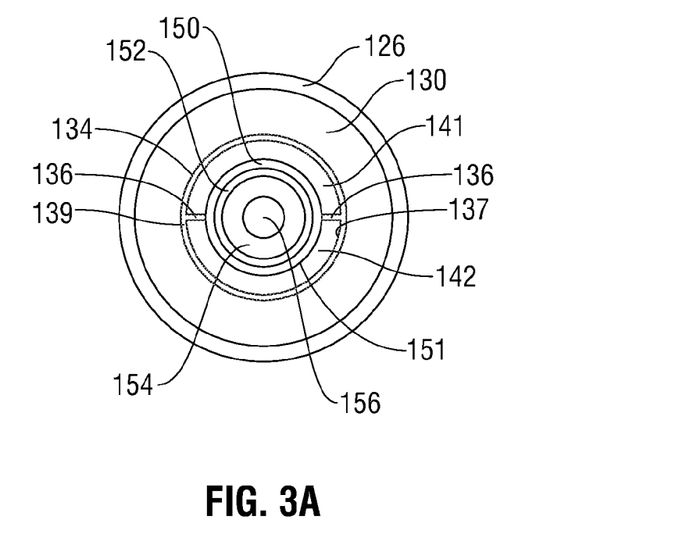
FIG. 3A shows a section view of the cooled surgical ablation probe of FIG. 2.
Figure 5A:
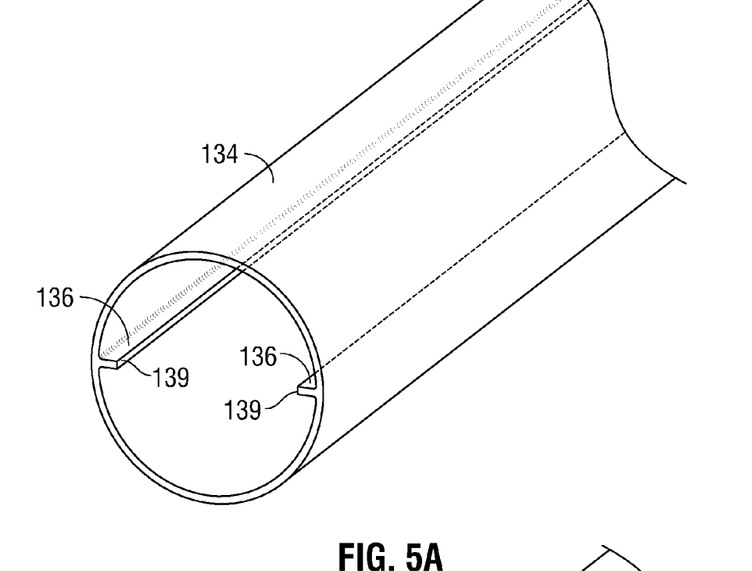
FIG. 5A shows a detail, perspective view of a hypotube in accordance with the present disclosure.
Figure 5B:
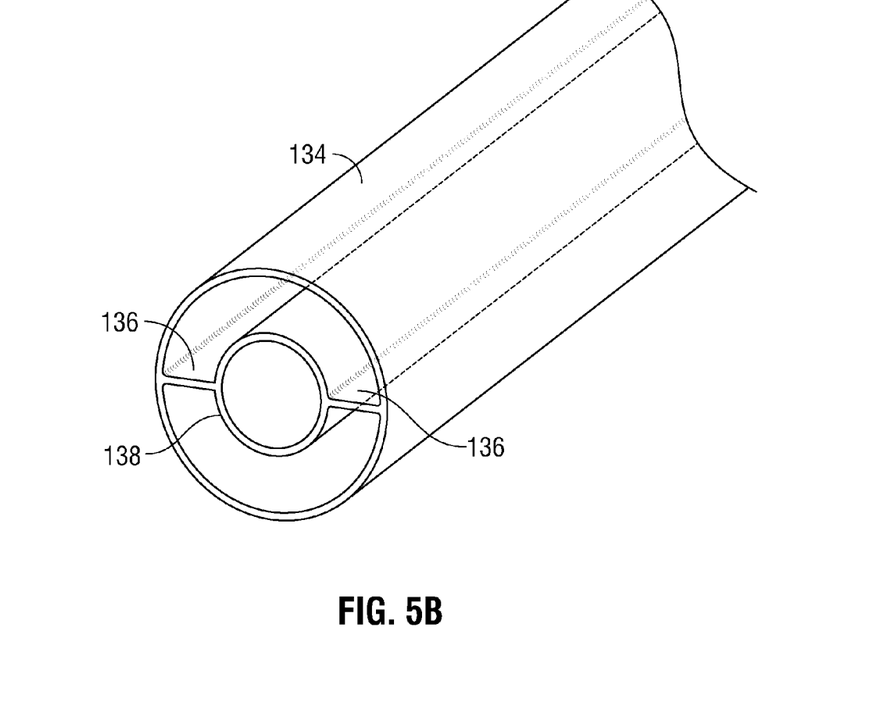
FIG. 5B shows a detail, perspective view of another hypotube in accordance with the present disclosure.

A tubular hypotube 134 is positioned coaxially around feedline 110 to form one or more fluid channels 141, 142. Hypotube 134 extends from a proximal end of the probe 10 to the feed point seal 135. Hypotube 134 includes one or more dividing ribs 136 (FIG. 3A) positioned longitudinally along an inner surface 137 of hypotube 134. Dividing ribs 136 are dimensioned to extend from an inner surface 137 of hypotube 134 to an outer surface 151 of outer sheath 150 of feedline 110, as seen in FIGS. 3A and 5A. Inner edge 139 of rib 136 is adapted to engage the outer sheath 150 of feedline 110. In an embodiment, ribs 136 are dimensioned to press into outer sheath 150 to form a fluid-tight seal. Additionally or alternatively, hypotube 134 may have a double-walled construction as best seen in FIG. 5B, wherein ribs 136 extend inwardly to an inner hypotube tube 138 concentrically positioned therein. Inner hypotube 138 has an inner diameter dimensioned to receive feedline 110, e.g., the inner diameter of inner hypotube 138 is about equal to the outer diameter of outer sheath 150.

Hypotube 134 and ribs 136 (as arranged around outer sheath 150 and/or inner hypotube 138) define a fluid inflow channel 141 and a fluid outflow channel 142, each having a proximal end and a distal end. A proximal end of fluid inflow channel 141 may be in operable fluid communication with a source of coolant 18, such as without limitation, saline and/or deionized water. A proximal end of fluid outflow channel 142 may be configured to expel spent coolant. Additionally or alternatively, outflow channel 142 may be configured to direct spent fluid to a reservoir (not explicitly shown), and/or to direct coolant to a circulator for re-use.

Figure 3B:
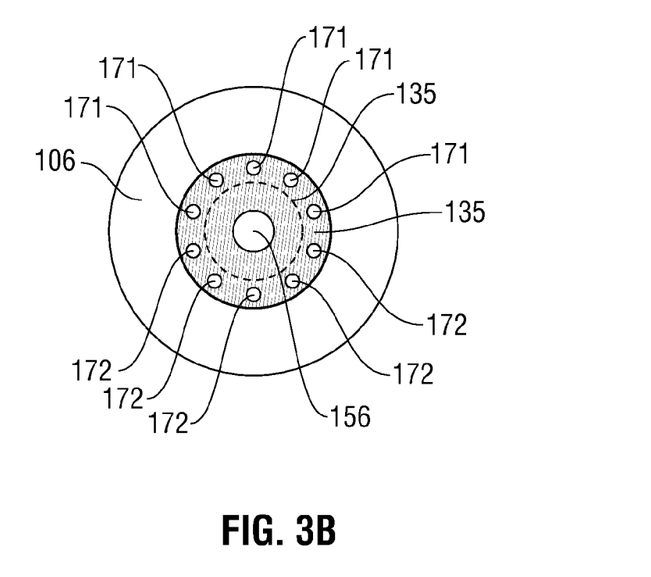
FIG. 3B shows another section view of the cooled surgical ablation probe of FIG. 2.
Figure 3C:
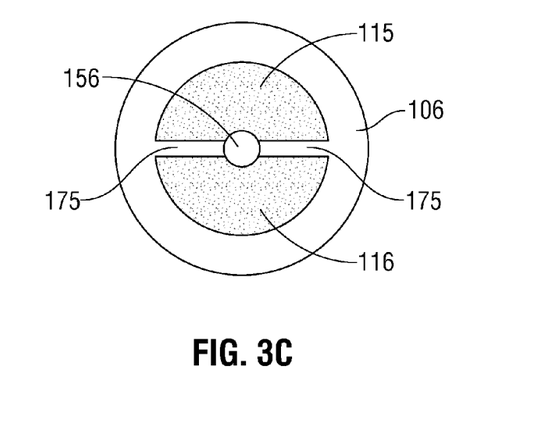
FIG. 3C shows yet another section view of the cooled surgical ablation probe of FIG. 2.

Continuing with reference to FIG. 3B, feed point seal 135 is positioned at a distal end 143 of hypotube 134. Feed point seal 135 includes one or more inflow holes 171 and/or outflow holes 172 defined therein that are adapted to permit the passage of coolant through feed point seal 135. Inflow holes 171 are positioned at a distal end of inflow channel 141 and are adapted to direct coolant to flow from inflow channel 141 into an inflow region 115 of porous core 114. Outflow holes 172 are positioned at a distal end of outflow channel 142 and are adapted to direct coolant flow from an outflow region 116 of porous core 114 to outflow channel 142.

Figure 4:
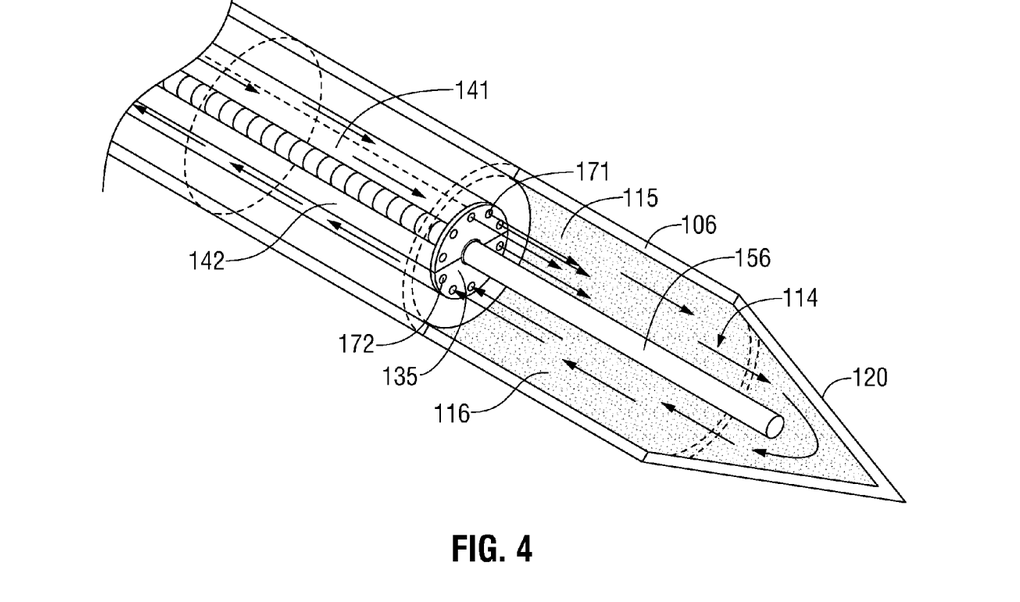
FIG. 4 shows a perspective view depicting coolant flow of an embodiment of cooled surgical ablation probe in accordance with the present disclosure.

As shown in FIG. 4, during use, coolant flows distally through inflow channel 141, through inflow holes 171, and into an inflow region 115 of porous core 114. Coolant flows proximally from an outflow region 116 of porous core 114, through outflow holes 172, and continues proximally through outflow channel 142. Coolant circulating through porous core 114 in the described manner cools distal radiating section 105 and/or tip 120, and may dielectrically load ablation energy radiating from inner conductor 156 to tissue. Feed point seal 135 includes a center opening 157 defined therein that is configured to accommodate the passage of inner conductor 156 therethrough and to provide a fluid-tight seal to prevent leakage or backflow of coolant into coaxial feedline 110.

Feed point seal 135 is sealably coupled to hypotube 134 using any suitable manner of fluid sealing. Feed point seal 135 may additionally or alternatively form a fluid-tight seal around inner conductor 156. Feed point seal 135 may additionally or alternatively encapsulate a distal end of one or more of outer sheath 150, outer conductor 152, and/or dielectric layer 154, which may prevent electrical short circuiting therebetween. Feed point seal 135 may be formed by overmolding over a distal end 143 of hypotube 134, e.g., formed by molding feed point seal 135 in place thereby forming a fluid-tight seal between a distal end 143 of hypotube 134 and feed point seal 135. Feed point seal 135 may be formed from any suitable material that can withstand probe operating temperatures and that is electrically non-conductive, for example without limitation, polyether block amide, such as Pebax®, manufactured by The Arkema Group of Colombes, France; polyetherimide (PEI), such as Ultem® and/or Extem®, manufactured by SABIC Innovative Plastics of Saudi Arabia; and/or polyimide-based polymer, such as Vespel®, manufactured by E. I. du Pont de Nemours and Company of Wilmington, Delaware, United States.

Distal radiating section 105 includes an outer dielectric surface 106 and a porous core 114 therein. Porous core 114 may include an inflow region 115 and an outflow region 116 having a separator 175 disposed therebetween. One or more openings (not explicitly shown) may be defined within separator 175 to enable coolant to flow from inflow region 115 to outflow region 116. Porous core 114 may be formed from any suitable material that provides radial support to outer dielectric surface 106 and that enables coolant perfusion within porous core 114. For example, and without limitation, porous core 114 may be formed from a porous ceramic material having an open cell, closed cell, tangle fiber network, and/or membrane structure. In an embodiment, porous core 114 may be formed from a metallic material, such as without limitation, stainless steel, titanium, nickel, nickel alloys, and bronze formed by any suitable manner of manufacture, e.g., powder compaction sintering, gravity sintering, powder rolling and sintering, isostatic compaction and sintering, metal spraying, metal coating and sintering, metal injection molding and sintering, and/or any other suitable manner of porous metal forming.

As best illustrated in FIG. 2, probe 10 includes a substantially cylindrical dielectric choke 130 concentrically disposed about a proximal portion of hypotube 134 wherein an inner diameter of dielectric choke 130 is about equal to an outer diameter of hypotube 134. Dielectric choke includes a distal portion 131 that has an outer diameter about equal to the outer diameter of distal radiating section 105, and includes a proximal portion 132 that has an outer diameter about equal to an inner diameter of a tubular choke outer jacket 126. Choke outer jacket 126 may be formed from any suitable heat-resistant metallic material, e.g., stainless steel. Dielectric choke 130 may be formed from material having low electrical conductivity at probe operating frequencies, e.g., elastomeric polymers, epoxy-fiber composites, and the like. A distal end 131 of dielectric choke 130 is joined to a proximal end 117 of outer dielectric surface 106. Hypotube 134 extends distally beyond a distal end 131 of dielectric choke 130 and/or extends distally beyond a proximal end 117 of outer dielectric surface 106 such that feed point seal 135 is positioned within outer dielectric surface 106 at a point distally of proximal end 117 of outer dielectric surface 106.

An outer surface of the probe 10, e.g., an outer surface of choke outer jacket 126, dielectric choke 130, dielectric surface 106, and/or tip 120, may include a dielectric coating (not explicitly shown). The dielectric coating may be formed from any suitable material having the ability to withstand the operating temperature of the probe and having a low electrical conductivity at probe operating frequencies, such as without limitation, polytetrafluoroethylene (a.k.a. PTFE or Teflon®, manufactured by the E.I. du Pont de Nemours and Co. of Wilmington, Del., USA), polyethylene tephthalate (PET), or the like. Additionally or alternatively, an outer surface of the probe 10 as previously described may include a heat shrink covering, such as polyolefin tubing, or any suitable heat-shrink material. The dielectric coating and/or heat shrink covering may provide a lubricious interface between the probe 10 and tissue to reduce or prevent undesirable adhesion of tissue to the probe 10, and to aid insertion of the probe 10 into tissue.

A method of manufacturing an ablation probe 10 in accordance with the present disclosure includes the steps of providing a hypotube 134 having one or more longitudinal ribs 136 extending radially inward from an inner surface 137 thereof. Hypotube 134 and/or ribs 136 may be formed by any suitable manner of manufacture, including without limitation by extrusion and/or welding. Hypotube 134 may be constructed by joining two or more semicircular sections (not explicitly shown) along a common longitudinal edge thereof to form the generally tubular shape of hypotube 134. A coaxial feedline 110 may be provided, wherein the feedline includes (in coaxial arrangement) an outer sheath 150, an outer conductor 152, an inner conductor 156, and a dielectric 154 disposed between the outer conductor 152 and the inner conductor 156, wherein the inner conductor 156 extends distally beyond the outer sheath 150, the outer conductor 152, and the dielectric 154. The inner conductor 156 may be extended by stripping outer sheath 150, outer conductor 152, and dielectric 154 as will be familiar to the skilled artisan.

Hypotube 134 is mounted over the feedline 110 to form one or more fluid channels defined between an inner surface 137 of hypotube 134, the one or more ribs 136, and an outer surface of the sheath (not explicitly shown). A distal end 143 of hypotube 134 is substantially aligned with a distal end of outer sheath 150, outer conductor 152, and/or dielectric 154. A feed point seal 135 may be mounted at a distal end of at least one of the sheath 150, the outer conductor 152, or the dielectric 154. The feed point seal 135 may be formed in place by overmolding whereby the sheath 150, the outer conductor 152, and/or the dielectric 154 are encapsulated within the feed point seal 135. During the overmolding step, the inner conductor 156 extends distally through the feed point seal 135. In this manner, a fluid-tight seal may be formed between inner conductor 156 and feed point seal 134.

A proximal end of porous core 114 is mounted to a distal end of the feed point seal 135. Porous core 114 may be mounted within distal radiating section 105 and/or tip 120. Porous core 114 may additionally or alternatively be formed within distal radiating section 105 and/or tip 120, and mounted to a distal end of the feed point seal. Feed point seal 135 may additionally or alternatively be overmolded over the combination of feedline 110 (including without limitation sheath 150, outer conductor 152, dielectric 154, and/or inner conductor 156) and porous core 114.

The described embodiments of the present disclosure are intended to be illustrative rather than restrictive, and are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. An ablation probe, comprising:
   a coaxial feedline having an outer sheath, an outer conductor, an inner conductor, and a dielectric disposed between the outer conductor and the inner conductor, wherein the inner conductor extends distally beyond the outer sheath, the outer conductor, and the dielectric;
   a hypotube coaxially disposed around the feedline having two longitudinal ribs that extend radially inward from an inner surface of the hypotube to an outer surface of the feedline to define an inflow fluid channel and an outflow fluid channel;
   a feed point seal operably coupled to a distal end of the hypotube and including a first opening and a second opening defined therethrough, each having a proximal end and a distal end, wherein the proximal end of the first opening is disposed in fluid communication with the inflow fluid channel and the proximal end of the second opening is disposed in fluid communication with the outflow fluid channel;
   a distal radiating section having a cylindrical outer dielectric surface, and a generally conical tip disposed at a distal end of the distal radiating portion, the cylindrical outer dielectric surface and the conical tip defining a cooling region therein; and
   a porous core closed within the cooling region and in fluid communication with the distal end of the first opening of the feed point seal and the distal end of the second opening of the feed point seal.

2. The ablation probe in accordance with claim 1, wherein the inner conductor extends distally through a third opening defined in the feed point seal.

3. The ablation probe in accordance with claim 1, wherein the inner conductor extends distally into the porous core.

4. The ablation probe in accordance with claim 1, wherein the feed point seal is formed from material selected from the group consisting of polyether block amide, polyetherimide, and polyimide-based polymer.

5. The ablation probe in accordance with claim 1, wherein the feed point seal encapsulates a distal end of at least one of the outer sheath, the outer conductor, and the dielectric.

6. The ablation probe in accordance with claim 1, wherein the porous core includes a separator adapted to define an inflow region of the porous core and an outflow region of the porous core.

7. The ablation probe in accordance with claim 6, wherein the inflow region and the outflow region are disposed in fluid communication through a separator opening defined in the separator.

8. The ablation probe in accordance with claim 1, wherein the porous core is formed from material selected from the group consisting of porous metal and porous ceramic.

9. The ablation probe in accordance with claim 1, further comprising a dielectric choke concentrically disposed around at least a portion of the hypotube.

10. The ablation probe in accordance with claim 9, where the dielectric choke includes an outer jacket concentrically disposed around at least a portion thereof.

11. An ablation system, comprising:
    a source of microwave ablation energy;
    a source of coolant;
    a coaxial feedline operatively coupled to the source of microwave ablation energy, wherein the coaxial feedline includes an outer sheath, an outer conductor, an inner conductor, and a dielectric disposed between the outer conductor and the inner conductor, wherein the inner conductor extends distally beyond the outer sheath, the outer conductor, and the dielectric;
    a hypotube operatively coupled to the source of coolant wherein the hypotube is coaxially disposed around the feedline and includes at least two longitudinal ribs that extend radially inward from an inner surface of the hypotube to an outer surface of the feedline to define an inflow fluid channel and an outflow fluid channel;
    a feed point seal operably coupled to a distal end of the hypotube and including a first opening and a second opening defined therethrough, each having a proximal end and a distal end, wherein the proximal end of the first opening is disposed in fluid communication with the inflow fluid channel and the proximal end of the second opening is disposed in fluid communication with the outflow fluid channel;
    a distal radiating section having a cylindrical outer dielectric surface, and a generally conical tip disposed at a distal end of the distal radiating portion, the cylindrical outer dielectric surface and the conical tip defining a cooling region therein; and
    a porous core closed within the cooling region and in fluid communication with the distal end of the first opening of the feed point seal and the distal end of the second opening of the feed point seal.

12. The ablation system in accordance with claim 11, wherein the inner conductor extends distally through a third opening defined in the feed point seal.

13. The ablation system in accordance with claim 11, wherein the inner conductor extends distally into the porous core.

14. The ablation system in accordance with claim 11, wherein the feed point seal is formed from material selected from the group consisting of polyether block amide, polyetherimide, and polyimide-based polymer.

15. The ablation system in accordance with claim 11, wherein the feed point seal encapsulates a distal end of at least one of the outer sheath, the outer conductor, and the dielectric.

16. The ablation system in accordance with claim 11, wherein the porous core includes a separator adapted to define an inflow region of the porous core and an outflow region of the porous core.

17. The ablation system in accordance with claim 16, wherein the inflow region and the outflow region are disposed in fluid communication through a separator opening defined in the separator.

18. A method of manufacturing an ablation probe, comprising the steps of:
- providing a hypotube having at least two longitudinal ribs that extend radially inward from an inner surface thereof;
- providing a coaxial feedline having in coaxial arrangement an outer sheath, an outer conductor, an inner conductor, and a dielectric disposed between the outer conductor and the inner conductor, wherein the inner conductor extends distally beyond the outer sheath, the outer conductor, and the dielectric;
- mounting the hypotube over the feedline to form an inflow fluid channel and an outflow fluid channel between an inner surface of the hypotube, the at least two ribs, and an outer surface of the sheath;
- forming a feed point seal at a distal end of at least one of the sheath, the outer conductor, or the dielectric;
- a distal radiating section having a cylindrical outer dielectric surface, and a generally conical tip disposed at a distal end of the distal radiating portion, the cylindrical outer dielectric surface and the conical tip defining a cooling region therein; and
- closing a porous core within the cooling region.

* * * * *